(12) United States Patent
Wakiyama

(10) Patent No.: US 8,907,797 B2
(45) Date of Patent: Dec. 9, 2014

(54) DRIVER MONITORING APPARATUS

(71) Applicant: DENSO CORPORATION, Kariya, Aichi-pref. (JP)

(72) Inventor: Kenichi Wakiyama, Kariya (JP)

(73) Assignee: DENSO CORPORATION, Kariya (JP)

( * ) Notice: Subject to any disclaimer, the term of this patent is extended or adjusted under 35 U.S.C. 154(b) by 222 days.

(21) Appl. No.: 13/723,681

(22) Filed: Dec. 21, 2012

(65) Prior Publication Data
US 2013/0162794 A1 Jun. 27, 2013

(30) Foreign Application Priority Data

Dec. 26, 2011 (JP) ................................ 2011-283890
Oct. 1, 2012 (JP) ................................ 2012-219531

(51) Int. Cl.
*G08B 23/00* (2006.01)
*G08B 21/02* (2006.01)
*A61B 5/18* (2006.01)
*B60K 28/06* (2006.01)
*G08B 21/06* (2006.01)
*A61B 5/11* (2006.01)

(52) U.S. Cl.
CPC . *G08B 21/02* (2013.01); *A61B 5/18* (2013.01); *B60K 28/06* (2013.01); *G08B 21/06* (2013.01); *A61B 5/1103* (2013.01); *A61B 5/1128* (2013.01); *B60K 28/066* (2013.01); *B60W 2420/42* (2013.01); *B60W 2540/26* (2013.01)
USPC ........ 340/576; 340/575; 340/425.5; 340/438; 340/439; 340/937; 701/51; 701/70

(58) Field of Classification Search
USPC .............. 340/575–576, 425.5, 438–439, 937; 701/51, 70
See application file for complete search history.

(56) References Cited

U.S. PATENT DOCUMENTS

| 6,822,573 | B2 * | 11/2004 | Basir et al. ..................... 340/575 |
| 7,649,445 | B2 * | 1/2010 | Kuramori et al. ............. 340/439 |
| 7,769,498 | B2 * | 8/2010 | Isaji et al. ......................... 701/1 |
| 8,229,603 | B2 * | 7/2012 | Miyata et al. ..................... 701/1 |
| 8,698,639 | B2 * | 4/2014 | Fung et al. ..................... 340/576 |

FOREIGN PATENT DOCUMENTS

| JP | 6262959 A | 9/1994 |
| JP | 8207617 A | 8/1996 |
| JP | 2009-009244 A | 1/2009 |
| JP | 2009244959 A | 10/2009 |
| JP | 4725254 B2 | 7/2011 |

OTHER PUBLICATIONS

Office Action mailed Feb. 25, 2014 issued in corresponding JP patent application No. 2012-219531 (and English translation).

* cited by examiner

*Primary Examiner* — Daniel Wu
*Assistant Examiner* — Son M Tang
(74) *Attorney, Agent, or Firm* — Posz Law Group, PLC

(57) ABSTRACT

A driver monitoring apparatus includes a detection section, a warning section and a changing operation section. The detection section detects at least one of a face direction and an eye direction of the driver, and generates a detection information regarding the at least one of the face direction and the eye direction detected. The warning section determines whether the driver has an inattentive drive by comparing the detection information to a reference information, and generates a warning when it is determined that the driver has the inattentive drive. The changing operation section receives an operation for changing the reference information, and changes a current reference information set before receiving the operation to a new reference information according to the operation received.

12 Claims, 9 Drawing Sheets

FIG. 4

| PARAMETER \ TYPE OF VEHICLE | COMPACT VEHICLE (LIGHT VEHICLE) | STANDARD-SIZED VEHICLE | TRUCK |
|---|---|---|---|
| BRIGHTNESS | SMALL (e.g. 1.5A) | MIDDLE (e.g. 2.0A) | LARGE (e.g. 2.5A) |
| ZOOM FACTOR | SMALL (e.g. 1.5 TIMES) | MIDDLE (e.g. 2 TIMES) | LARGE (e.g. 2.5 TIMES) |
| CONVERTED VALUE OF ELEVATION ANGLE | 20° | 25° | 30° |

DRIVER MONITORING APPARATUS

CROSS REFERENCE TO RELATED APPLICATION

This application is based on Japanese Patent Application No. 2011-283890 filed on Dec. 26, 2011 and No. 2012-219531 filed on Oct. 1, 2012, the disclosures of which are incorporated herein by reference.

TECHNICAL FIELD

The present disclosure relates to a driver monitoring apparatus that monitors an inattentive drive of a driver.

BACKGROUND

In general, a driver monitoring apparatus takes an image of a driver's face and recognizes an eye opening degree, an eye direction and a face direction of the driver by analyzing the image of the driver's face. The driver monitoring apparatus further monitors whether the driver drives properly, such as whether the driver keeps his eyes on the road and whether the driver does not fall asleep at the wheel, based on a result of recognition. Such a driver monitoring apparatus is described in JP4725254B2, for example.

In such a monitoring apparatus, when it is determined that the driver falls asleep at the wheel or drives inattentively, a warning sound is generated to alert the driver.

A conventional driver monitoring apparatus is optimized to each type of vehicle. However, different types of vehicles will have different widths, and hence a reference to determine an inattentive drive will be different depending on types of vehicles. Therefore, if the conventional driver monitoring apparatus optimized to one type of the vehicle is equipped to another type of vehicle, the conventional driver monitoring apparatus will not monitor the driver properly.

For example, it is proposed to determine an inattentive drive in left and right directions based on a driver's eye direction. When an angle of the driver's eye relative to a frontal direction is greater than a reference angle, which is defined between the frontal direction and an eye direction that the diver looks at a side mirror, that is, when the driver's eye direction moves in a left or right direction over the reference angle, the inattentive drive is determined. However, the reference angle is different depending on the width of the vehicle. Therefore, if the driver monitoring apparatus optimized to one type of vehicle is equipped to another type of vehicle, the inattentive drive will not be determined properly. As a result, a warning will be given each time the driver looks the side mirror due to the reference angle being too small, or a warning will not be given even if the driver's eye direction moves in a left or right direction over the side mirror.

Also, the similar drawbacks will arise when a driver's seating position is different even in the same type of vehicles.

SUMMARY

It is an object of the present disclosure to provide a driver monitoring apparatus that is capable of properly determining an inattentive drive and alerting the inattentive drive to a driver.

According to a first aspect of the present disclosure, a driver monitoring apparatus includes a detection section, a warning section and a changing operation section. The detection section detects at least one of a face direction of the driver and an eye direction of the driver, and generates a detection information regarding the at least one of the face direction and the eye direction detected. The warning section determines whether the driver has the inattentive drive by comparing the detection information to a reference information, and generates a warning when it is determined that the driver has the inattentive drive. The changing operation section receives an operation for changing the reference information, and changes a current reference information set before receiving the operation to a new reference information according to the operation received.

In the driver monitoring apparatus described above, the reference information as a reference for determining the inattentive drive of the driver can be flexibly changed according to a vehicle to which the driver monitoring apparatus is equipped. Therefore, even if the driver monitoring apparatus is equipped to any vehicle, the driver monitoring apparatus can properly determines an inattentive drive based on the reference information suitable for the vehicle, and warns the driver of the inattentive drive.

According to a second aspect of the present disclosure, a driver monitoring apparatus includes a detection section, a warning section and an operation section. The detection section detects at least one of a face direction and an eye direction of the driver, and generates a detection information regarding the at least one of the face direction and the eye direction detected. The warning section determines whether the driver has the inattentive drive by comparing the detection information to a reference information, and generates a warning when it is determined that the driver has the inattentive drive. The operation section receives an operation for setting the reference information, and sets the reference information according to the operation received. The reference information is different depending on a type of a vehicle to which the driver monitoring apparatus is equipped.

In the driver monitoring apparatus described above, an advantageous effect similar to the driver monitoring apparatus according to the first aspect will be achieved.

BRIEF DESCRIPTION OF THE DRAWINGS

The above and other objects, features and advantages of the present disclosure will become more apparent from the following detailed description made with reference to the accompanying drawings, in which like parts are designated by like reference numbers and in which:

FIG. 4 is a diagram for explaining imaging information set in the driver monitoring apparatus according to the embodiment;

DETAILED DESCRIPTION

Embodiments of the present disclosure will be described with reference to the drawings.

<Overall Structure>

Figure 1:
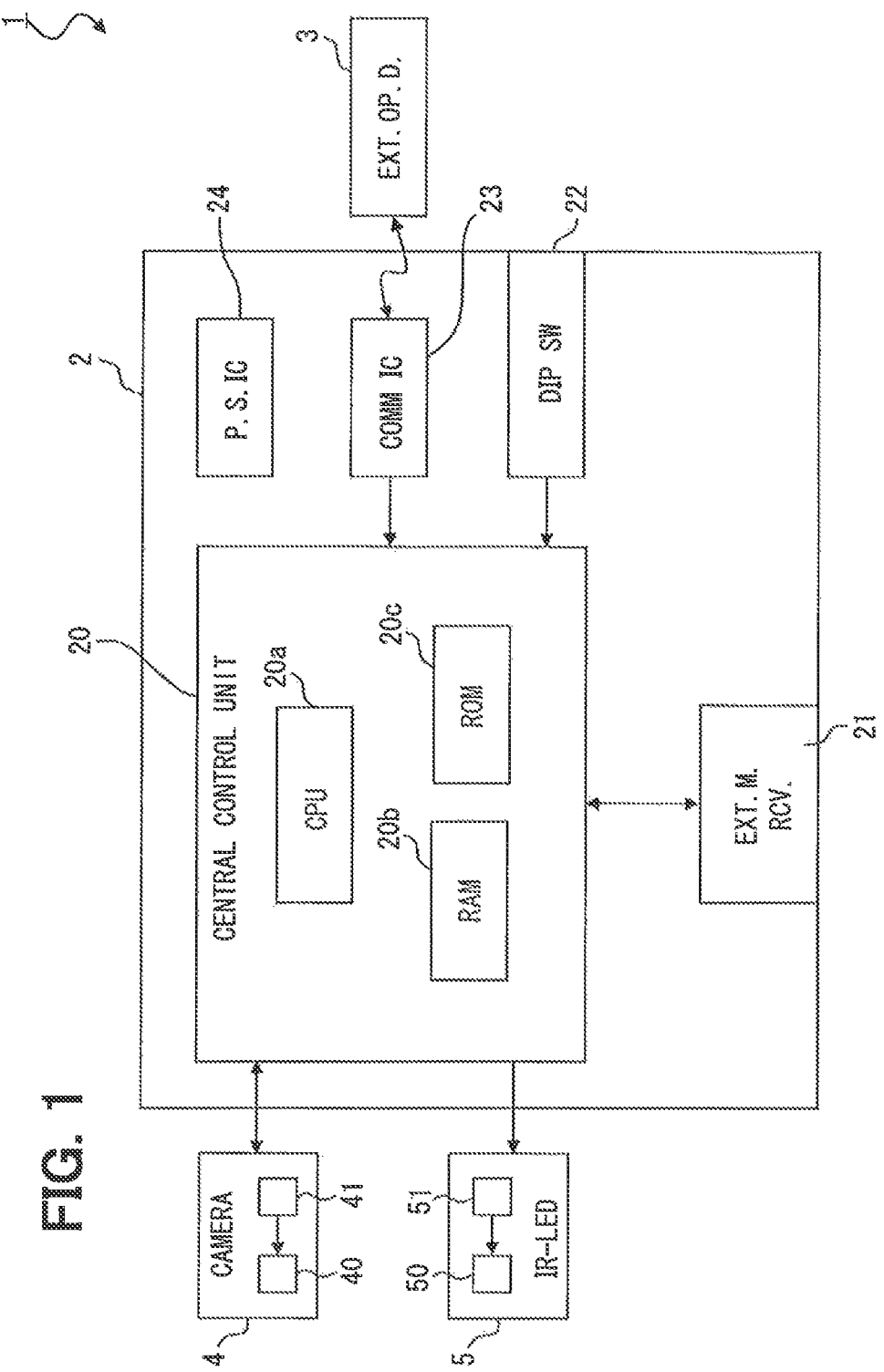
FIG. 1 is a block diagram of a driver monitoring apparatus according to an embodiment of the present disclosure.

Referring to FIG. 1, a driver monitoring apparatus 1 according to an embodiment includes a main device 2, an external operation device 3, a camera 4, and a light 5.

The main device 2 includes a central control unit 20 and an external memory receiving part 21. The central control unit 20 is provided by a computer including a CPU 20a, a RAM 20b, a ROM 20c and the like. The external memory receiving part 21 is configured to receive an external memory. The external memory receiving part 21 is configured such that the external memory is attached to and detached from the external memory receiving part 21. When the external memory is attached to the external memory receiving part 21, the external memory receiving part 21 allows communication between the central control unit 20 and the external memory.

The RAM 20b includes a volatile portion and a non-volatile portion. Reference information and imaging information, which will be described later, are stored in the non-volatile portion.

The ROM 20c is stored with relationship information, a program for performing an inattentive drive monitoring process, and the like. The relationship information indicates correlations between vehicle type information and the reference information and correlations between the vehicle type information and the imaging information. The vehicle type information includes information regarding types of vehicles, such as a compact vehicle (light vehicle), a standard-sized vehicle, a truck, a right-hand drive vehicle, a left-hand drive vehicle and any classifications of vehicles.

The main device 2 includes a dual in-line package (DIP) switch 22, a communication IC 23, and a power supply IC 24. The DIP switch 22 includes multiple switches (switching pieces) arranged on a housing (not shown) of the main device 2. The communication IC 23 performs a wireless communication with the external operation device 3. The power supply IC 24 distributes electric power supplied from a battery (not shown) of a vehicle to respective components of the main device 2, the camera 4 and the light 5.

The DIP switch 22 is a switch unit to specify a type of the vehicle to which the driver monitoring apparatus 1 is equipped. The external operation device 3 can perform the wireless communication with the main device 2 through the communication IC 23 when the external operation device 3 is inside of a predetermined communication area from the communication IC 23. The external operation device 3 is a device to specify the type of the vehicle to which the driver monitoring apparatus 1 is equipped.

The camera 4 is a CMOS camera, for example. The camera 4 is disposed on a steering column, The camera 4 is arranged such that an optical axis directs to a position generally corresponding to a driver's face seated on a driver's seat.

The camera 4 includes an imaging portion 40 and a magnification changing portion 41. The imaging portion 40 captures an image of a driver's face. The magnification changing portion 41 changes a magnification of the image captured by the imaging portion 40, such as a position of a lens, in accordance with an instruction from the central control unit 20.

The light 5 includes an infrared (IR)-LED 50 and a luminance changing portion 51. The light 5 applies a near-infrared light emitted from the IR-LED 50 toward the driver's face. The light 5 is integrated with the camera 4.

The luminance changing portion 51 changes a luminance of the IR-LED 50 in accordance with an instruction from the central control unit 20.

<Inattentive Drive Monitoring Process>

Figure 2:
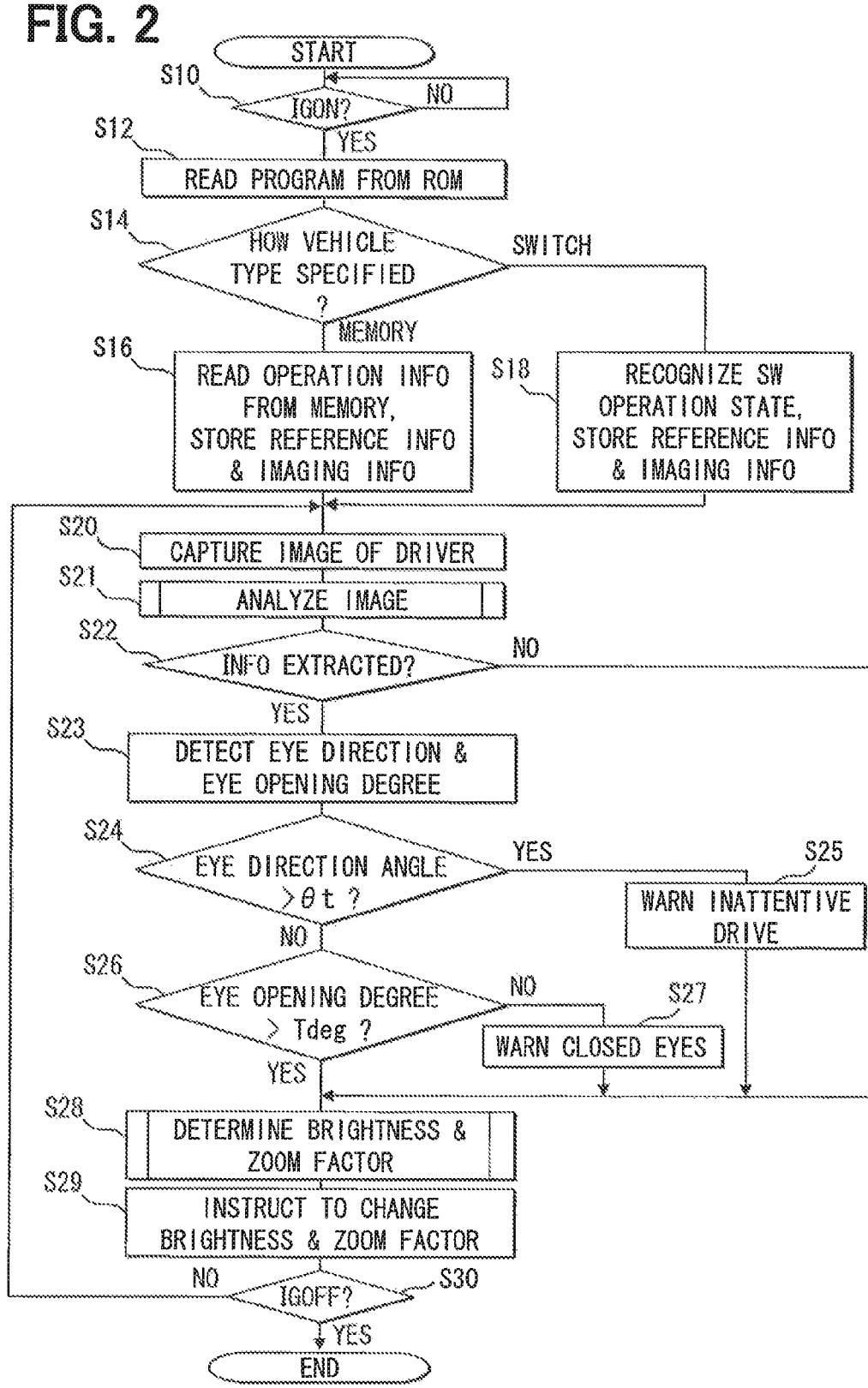
FIG. 2 is a flowchart of an inattentive drive monitoring process performed by a central control unit of the driver monitoring apparatus according to the embodiment.

Next, an inattentive drive monitoring process performed by the CPU 20a of the central control unit 20 will be described with reference to FIG. 2.

In the following description, the inattentive drive monitoring process will be performed in ascending order of step numbers in the absence of specific explanation.

At S10, it is determined whether an ignition switch is turned on. Namely, the inattentive drive monitoring process waits until the ignition switch is turned on.

When it is determined that the ignition switch is turned on (S10: Yes), a program for performing the inattentive drive monitoring process is read from the ROM 20c at S12, and the following process is performed according to the program read from the ROM 20c.

At S14, it is determined how the type of the vehicle is specified. In the present embodiment, the type of the vehicle is specified by operating one of the DIP switch 22 and the external operation device 3. Therefore, at S14, it is determined whether the type of vehicle is specified by operation of the DIP switch 22 or operation of the external operation device 3.

Determination information as a basis for the determination of S14 is stored in the external memory attached to the external memory receiving part 21. The determination of S14 is made based on the determination information stored in the external memory. The determination information is stored in the external memory by an operation information transmitting process, which will be described later.

It is to be noted that the determination of S14 may be made based on a presence of operation of a switch disposed in the housing of the main device 2, or may be made based on any other way.

When it is determined that the type of the vehicle is specified by the operation of the external operation device 3 (S14: memory), the process proceeds to S16. When it is determined that the type of the vehicle is specified by the operation of the DIP switch 22 (S14: switch), the process proceeds to S18.

The external memory is stored with information regarding the type of the vehicle to which the driver monitoring apparatus 1 is equipped, as operation information inputted by operating the external operation device 3. In a case where the type of the vehicle is specified by the operation of the external operation device 3 (S14: memory), the reference information and the imaging information that correspond to the type of the vehicle indicated by the operation information are searched from the information stored in the ROM 20*c*, and the searched reference information and the searched imaging information are stored in the RAM 20*b*, at S16.

In a case where the type of the vehicle to which the driver monitoring apparatus 1 is equipped is specified by the operation of the DIP switch 22 (S14: switch), the type of the vehicle is specified based on a combination of operation state of the switching pieces of the DIP switch 22 at S18. In this case, the reference information and the imaging information that correspond to the type of the vehicle indicated by the combination of the operation states of the DIP switch 22 are searched from the information stored in the ROM 20*c*. Further, the searched reference information and the searched imaging information are stored in the RAM 20*b*.

At S16 and S18, when the reference information and the imaging information have been already stored in the RAM 20*b*, these reference information and imaging information are cancelled, and the searched reference information and the searched imaging information are stored as new reference information and new imaging information.

Figure 3:
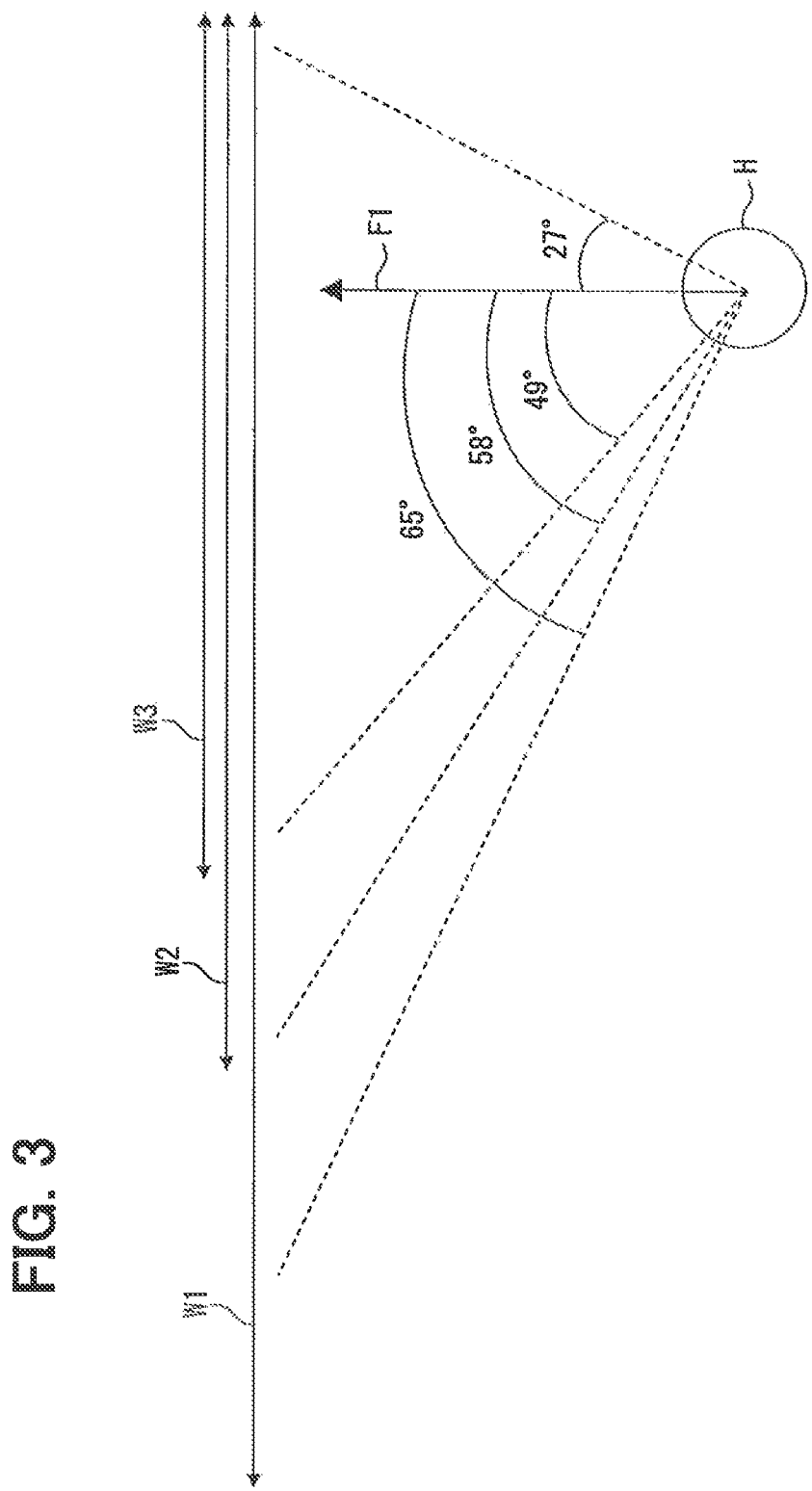
FIG. 3 is a diagram for explaining reference information set in the driver monitoring apparatus according to the embodiment.

The reference information is information regarding a threshold used for detecting an angle of the driver's eye direction defined in a horizontal direction, such as left and right directions, relative to a frontal direction of the driver seated on the driver's seat, as shown in FIG. 3. In FIG. 3, an arrow W1 denotes a width of a truck, an arrow W2 denotes a width of a standard-sized vehicle, and an arrow W3 denotes a width of a compact vehicle. Also, an arrow F1 denotes the frontal direction, and H denotes a driver's head As the threshold, in a case of a right-hand drive vehicle, for example, a right-side threshold is 27 degrees to the right direction from the frontal direction F1 for all types of vehicles, A left-side threshold for a compact vehicle is 49 degrees to the left direction from the frontal direction F1. A left-side threshold for a standard-sized vehicle is 58 degrees to the left direction from the frontal direction. Also, a left-side threshold for a truck is 65 degrees to the left direction from the frontal direction F1.

The imaging information is information regarding a zoom factor of the camera 4, a brightness of the light 5, and an elevation angle of the camera 4, which are applied according to the types of the vehicle, such as a compact vehicle, a standard-sized vehicle and a truck, as shown in FIG. 4.

The zoom factor of the camera 4 for the compact vehicle is the smallest, and the zoom factor of the camera 4 for the truck is the largest. For example, the zoom factor for the compact vehicle is 1.5 times, the zoom factor for the standard-sized vehicle is 2 times, and the zoom factor for the truck is 2.5 times, The brightness of the light 5 for the compact vehicle is the smallest and the brightness of the light 5 for the truck is the largest. For example, the brightness for the compact vehicle is 1.5 A, the brightness for the standard-sized vehicle is 2 A, and the brightness for the truck is 2.5 A.

The elevation angle of the camera 4 is an angle of elevation assumed when the camera 4 is equipped to the vehicle. The elevation angle of the camera 4 is the smallest for the compact vehicle and is the largest for the truck. For example, the elevation angle for the compact vehicle is 20 degrees, the elevation angle for the standard-size vehicle is 25 degrees, and the elevation angle for the truck is 30 degrees.

The imaging information is set at a time of beginning the inattentive drive monitoring process because of the following reasons.

Figure 5A:
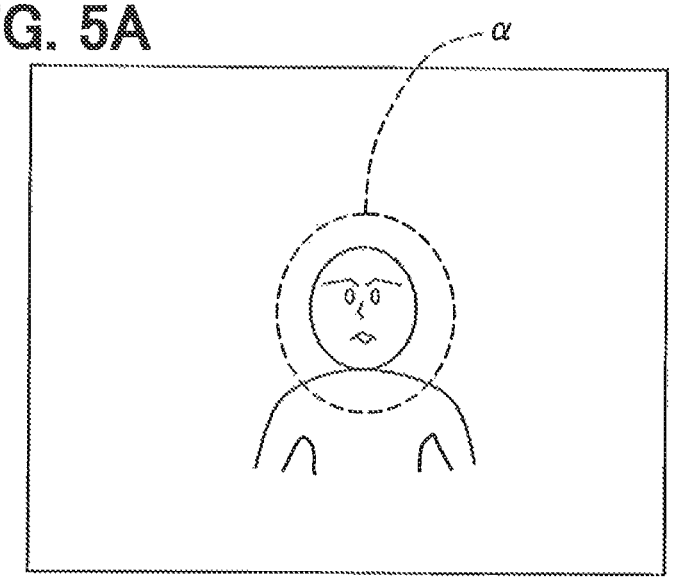
FIG. 5A is a schematic diagram of an image of a driver captured in a truck by a camera that has a zoom factor for a compact vehicle.
Figure 5B:
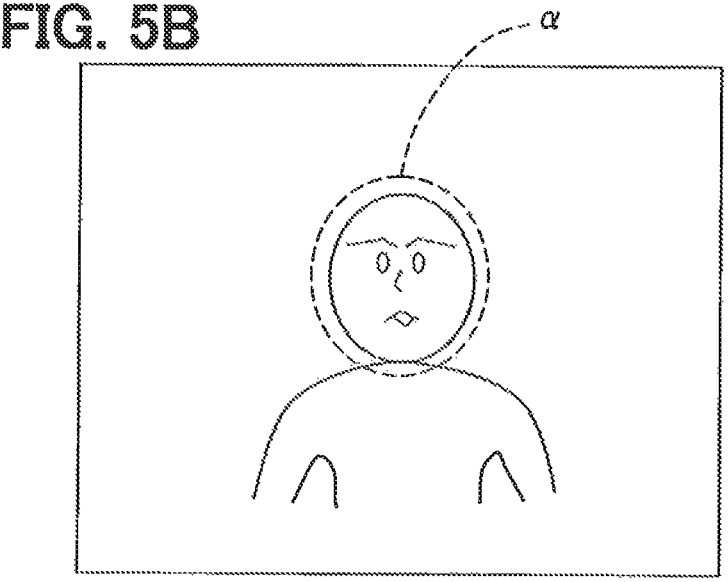
FIG. 5B is a schematic diagram of an image of a driver captured in a compact vehicle by a cameral that has a zoom factor for the compact vehicle.

If the zoom factor of the camera 4 is set only for the compact vehicle, in a case of the compact vehicle, as shown in FIG. 5B, the driver's face may be captured in substantially the same area as an assumed face size area a where a driver's face is assumed to be displayed when the image of the driver's face is captured by the camera 4.

In a case of the truck, however, a distance between the camera 4 and the driver's face is generally greater than a distance between the camera 4 and the driver's face in the compact vehicle. Therefore, the size of the driver's face captured in the image is likely to be small, as shown in FIG. 5A. As such, the area of the driver's face captured in the image is much smaller than the assumed face size area α.

As described above, if the area of the driver's face is too small in the image captured by the camera 4, it is difficult to properly recognize an outline of the face, such as outlines of eyes and nose and an overall outline of the face, in the process at and after S20. As a result, accuracy of analyzing the driver's face is likely to reduce. Similarly, if the area of the driver's face is too large in the image captured by the camera 4, the accuracy of analyzing the driver's face is likely to reduce.

The zoom factor is adjusted in the process at and after S20. However, if the zoom factor is very different, it takes time to adjust the zoom factor in the process at and after S20. In the present embodiment, therefore, a basic zoom factor is set according to the type of the vehicle before S20.

With regard to the brightness of the light 5, a distance between the light 5 and the driver in the compact vehicle is smaller than a distance between the light 5 and the driver in the standard-sized vehicle. Therefore, if the brightness of the light 5 is set only for the standard-sized vehicle, the near-infrared light applied to the driver is too bright. As a result, the outline of the face is blurred in the compact vehicle, as shown in FIG. 5A.

Figure 6A:
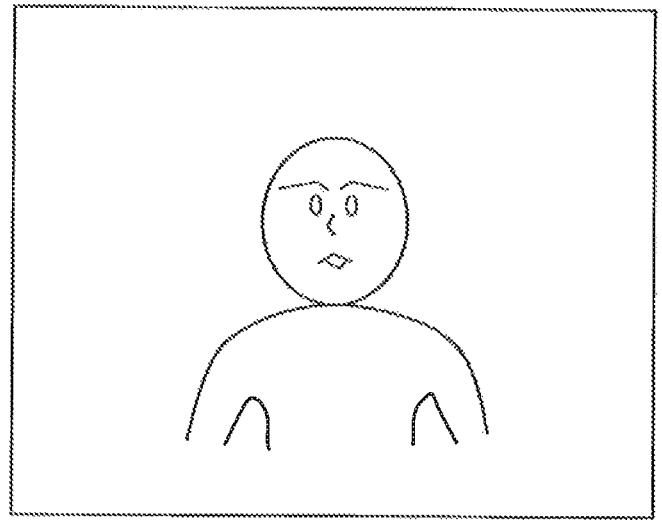
FIG. 6A is a schematic diagram of an image of a driver captured in a compact vehicle by a camera with a brightness of a near-infrared light for a standard-sized vehicle.
Figure 6B:
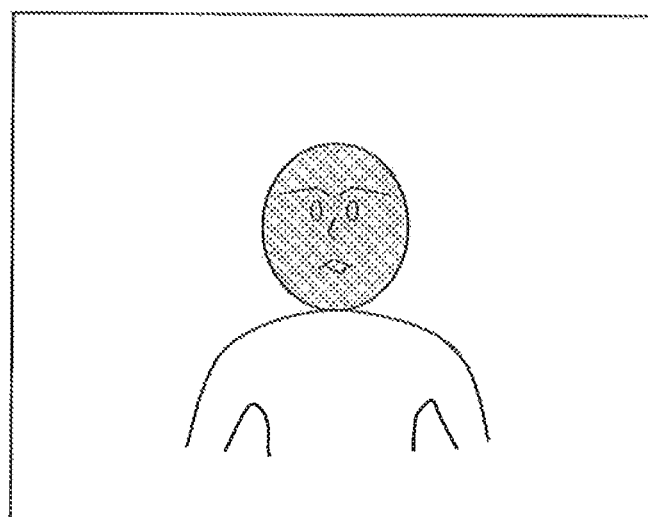
FIG. 6B is a schematic diagram of an image of a driver captured in a truck by a camera with a brightness of a near-infrared light for a standard-sized vehicle.

On the other hand, the distance between the light 5 and the driver in the truck is further than the distance between the light 5 and the driver in the standard-sized vehicle. Therefore, if the brightness of the light 5 is set only for the standard-sized vehicle, the near-infrared light applied to the driver is too dark. As a result, the outline of the face is covered, as shown in FIG. 6B.

As described above, if the brightness of the near-infrared light is not set to a proper brightness, it is difficult to properly recognize the outline of the face, such as outlines of eyes and nose and an overall outline of the face, in the process at and after S20. As a result, accuracy of analyzing the face of the driver is likely to reduce.

In the process at and after S20, the brightness of the near-infrared light is adjusted. However, if the brightness is very different, it takes time to adjust the brightness. In the present embodiment, therefore, a basic brightness is set according to the type of the vehicle before S20.

When the driver's face is captured by the camera 4, positions of the driver's eyes and nose are estimated based on the set elevation angle. If the elevation angle is not set or is erroneously set, it takes time to detect the positions of the driver's eyes and nose.

Figure 7A:
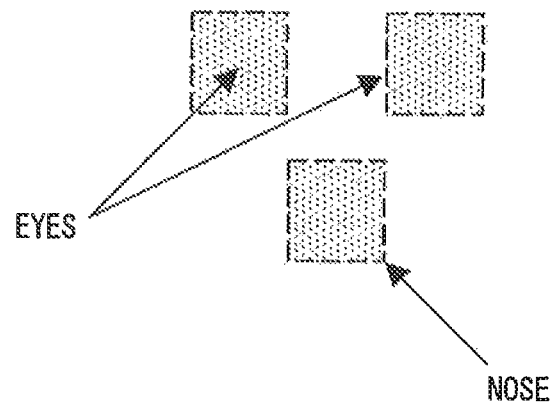
FIG. 7A is a schematic diagram for illustrating positions of driver's eyes and nose when an image of a driver's face is captured in a compact vehicle by a camera set at an elevation angle of 20 degrees.
Figure 7B:
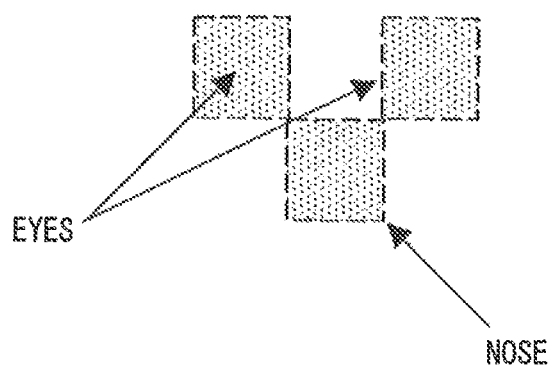
FIG. 7B is a schematic diagram for illustrating positions of driver's eyes and nose when an image of a driver's face is captured in a truck by a camera set at an elevation angle of 30 degrees.
Figure 8A:
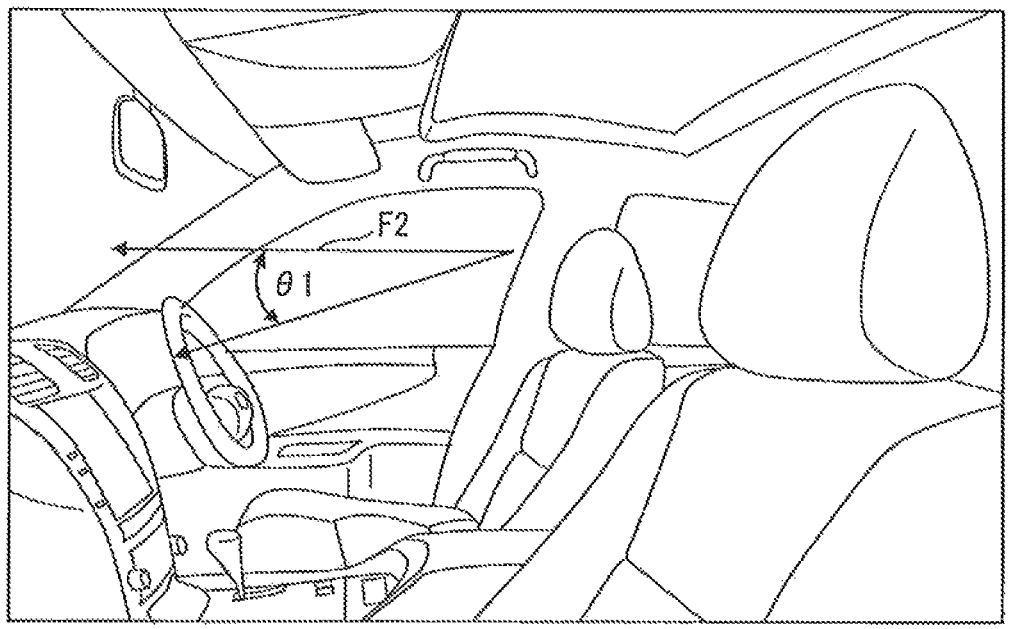
FIG. 8A is a schematic diagram of an image of an interior of a standard-sized vehicle for explaining an elevation angle of imaging information and a determination threshold for an inattentive drive in a vertical direction.

FIG. 7A illustrates a positional relationship between the diver's eyes and the driver's nose captured by the camera 4 in the compact vehicle, and FIG. 7B illustrates a positional relationship between the driver's eyes and the driver's nose captured by the camera 4 in the truck. As shown in FIGS. 7A and 7B, the positional relationship between the driver's eyes and the driver's nose is different depending on the type of the vehicle due to the difference of the elevation angle. Namely, as shown in FIGS. 8A and 86, the elevation angle in the truck is greater (deeper) than the elevation angle in the compact vehicle.

If it is difficult to realize the positional relationship between the driver's eyes and the driver's nose, it is difficult to recognize the outline of the face, such as the outlines of eyes and nose and the overall outline of the face, in the process at and after S20. As a result, accuracy of analyzing the driver's face reduces.

In the present embodiment, therefore, the information regarding the elevation angle is set according to the type of the vehicle before S20.

Referring back to FIG. 2, at S20, the image of the drive's face is captured using the camera 4 and the light 5. The process from S20 to S29 is performed every approximately 33 milliseconds or every imaging frame so as to monitor the driver and so as to adjust the zoom factor of the camera 4 and the brightness of the light 5.

At S21, the image captured at S20 is analyzed. For example, the position of the nose is identified in the assumed face size area a in the image, and the positions of the eyes are estimated based on the position of the nose using the information on the elevation angle. Further, the eyes are identified in an area including the estimated positions. Then, the outlines of the eyes and the outline of the nose are analyzed from the image around the positions of the eyes and nose identified. Further, the outline of the face is extracted from the area including the entirety of the identified eyes and nose, and information on the brightness and the like in the extracted outline are extracted.

At S22, it is determined whether the outlines of the eyes and nose and the outline of the face have been extracted in the analysis of S21. When the outlines have not been extracted (S22: No), the process proceeds to S28, When the outlines have been extracted (S22; Yes), the process proceeds to S23.

At S23, the eye direction of the driver and an opening degree of the driver's eye are detected based on the information on the outlines of the eyes and nose and the outline of the face extracted at S21. At S24, it is determined whether the angle of the eye direction of the driver is greater than a threshold angle ($\theta_t$) indicated by the reference information by comparing information regarding the eye direction detected at S23 to the reference information.

When it is determined that the angle of the eye direction is greater than the threshold angle ($\theta_t$) at S24, the process proceeds to S25. When it is determined that the angle of the eye direction is equal to or less than the threshold angle ($\theta_t$) at S24, the process proceeds to S26, At S25, a warning is generated by means of a speaker or a buzzer to warn the driver of the inattentive drive. At S26, it is determined whether the opening degree of the driver's eye is greater than a predetermined opening degree (threshold $T_{deg}$). When it is determined that the opening degree of the driver's eye is equal to or less than the predetermined opening degree ($T_{deg}$), the process proceeds to S27. When it is determined that the opening degree of the driver's eye is greater than the predetermined opening degree ($T_{deg}$), the process proceeds to S28. At S27, a warning is generated by means of a speaker or a buzzer to warn the driver of his/her eyes being closed for a time or he/she falling asleep.

At S28, it is determined whether the size of the outline of the driver's face is the maximum within the assumed face size area α, based on information on the size of the outline of the driver's face extracted by the analysis at S21. That is, it is determined whether the size of the outline of the driver's face is appropriate to determine the outlines of the driver's eyes and nose and the outline of the driver's face.

At S28, it is also determined whether the brightness of the driver's face is appropriate to determine the eye direction of the driver and the direction of the driver's face based on information on the brightness of the driver's face extracted by the analysis at S21. That is, it is determined whether the brightness of the driver's face within the outline is appropriate to determine the outlines of the driver's eyes and nose and the outline of the driver's face.

In this case, a reference brightness range for determining whether the brightness is appropriate is set beforehand. Therefore, when the brightness of the driver's face within the outline in the image captured at S20 is within the predetermined brightness range, it is determined that the brightness is appropriate. The predetermined brightness range is set such that the area of the captured image is not too dark, and not too bright.

When it is determined that the size of the driver's face is not appropriate at S28, an instruction to change the zoom factor is provided to the camera 4 at S29. Thus, the camera 4 changes the zoom factor in accordance with the instruction. For example, when the driver's face in the captured image is small, the zoom factor is increased by one level. Also, when the driver's face in the captured image is large, the zoom factor is reduced by one level.

In the present embodiment, the zoom factor is divided into precise levels. Therefore, when the zoom factor is changed at S29, the zoom factor is changed by one-by-one level. When it is determined that the brightness of the driver's face in the area of the outline is not appropriate at S28, an instruction to change the brightness of the near-infrared light is provided to the light 5 at S29. Thus, the light 5 changes the brightness in accordance with the instruction. For example, when the driver's face in the captured image is light, the brightness of the light 5 is reduced by one level, and when the brightness of the driver's face in the captured image is dark, the brightness of the light 5 is increased by one level In the present embodiment, the brightness of the light 5 is divided into precise levels. Therefore, at S29, the brightness of the light 5 is increased or decreased by one-by-one level. As described above, at S28 and S29, the zoom factor of the camera 4 and the brightness of the light 5 are suitably adjusted based on the analysis result at S21 so as to achieve a further accurate analysis result.

Therefore, even when the driver monitoring apparatus 1 of the present embodiment is equipped to any type of the vehicle, and even when the brightness of the driver's face and/or the distance of the driver's face from the camera 4 is changed due to a change in ambient brightness and/or a change in position of the driver, the image of the driver's face can be captured with the appropriate zoom factor and the appropriate brightness. Therefore, the analysis accuracy of the image further improves.

At S30, it is determined that the ignition switch is turned off. When it is determined that the ignition switch is not turned off (S30: No), the process returns to S20. When it is determined that the ignition switch is turned off (S30: Yes), the process is finished.

<Operation Information Transmitting Process>

Next, it will be described in regard to an operation information transmitting process for renewing the operation information stored in the external memory by operating the external operation device 3.

Figure 9:
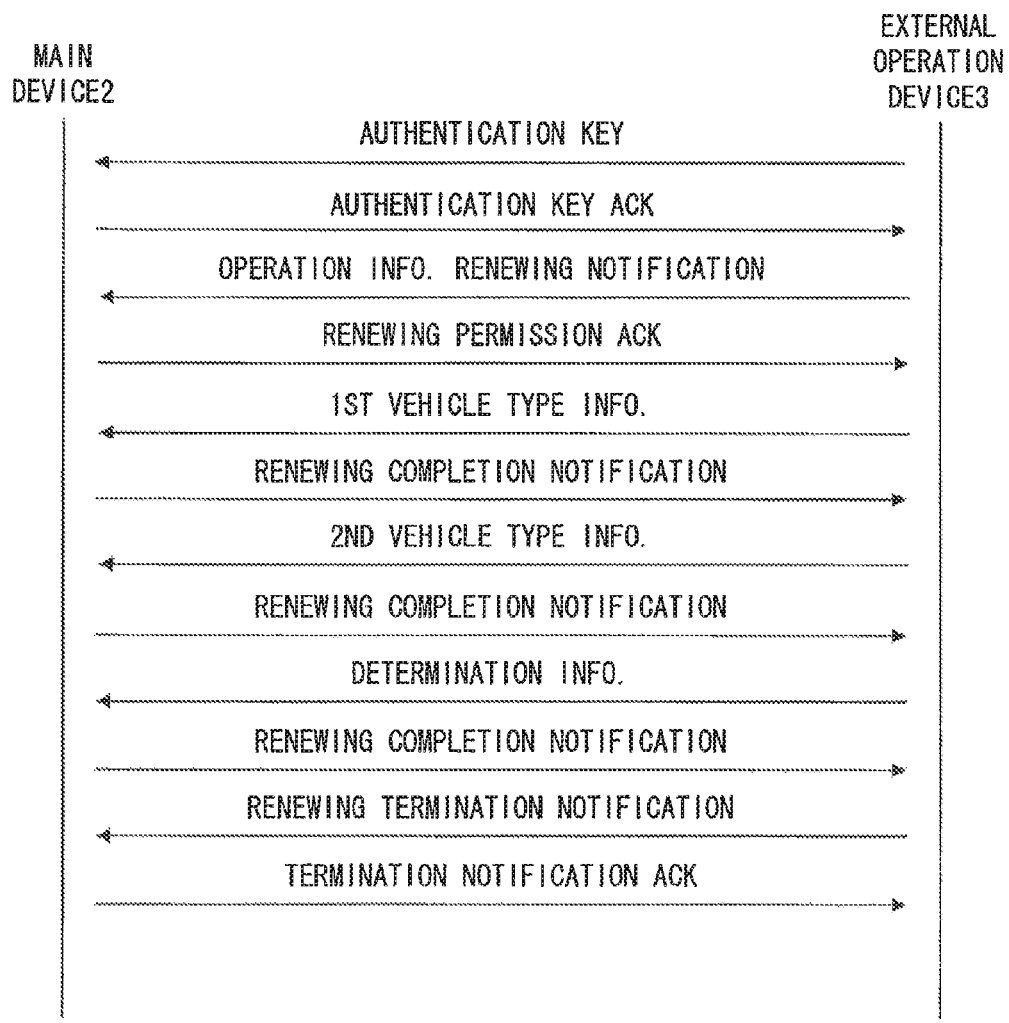
FIG. 9 is a time sequence chart of an operation information transmitting process performed for renewing operation information stored in an external memory in accordance with an operation of an external operation device of the driver monitoring apparatus according to the embodiment.

FIG. 9 is a time sequence chart of the operation information transmitting process.

The operation information transmitting process is performed when the external operation device 3 is in a communication state where the external operation device 3 can communicate with the communication IC 23.

The operation information transmitting process is begun when an authentication key is transmitted from the external operation device 3 to the main device 2. In the present embodiment, when the external operation device 3 is in the communication state, it is indicated on a monitor (not shown) of the external operation device 3 that the external operation device 3 is in the communication state. When the authentication key is inputted by operating an operation button or the like (not shown) of the external operation device 3 and a transmission instruction button or the like (not shown) of the external operation device 3 is pressed in a condition where the external operation device 3 is in the communication state, the authentication key is transmitted from the external operation device 3 to the main device 2.

The main device 2 has a function of authenticating the authentication key. Therefore, when the main device receives the authentication key through the communication IC 23, and authenticates the authentication key, the main device 2 transmits an acknowledgement signal indicating an acknowledgement of the authentication key (authentication key ACK) to the external operation device 3 for permitting a renewing process for renewing the operation information stored in the external memory.

After the external operation device 3 receives the authentication ACK, when an operation for notifying of renewing of the operation information is performed through a button (not shown) of the external operation device 3, a notification signal for notifying of the renewing of the operation information is transmitted from the external operation device 3 to the main device 2.

When the main device 2 receives the notification signal, the main device 2 transmits an acknowledgement signal indicating the renewing being permitted (renewing permission ACK) to the external operation device 3. When the external operation device 3 receives the rewriting permission ACK, a process of transmitting information for renewing the operation information stored in the external memory from the external operation device 3 to the main device 2 is performed thereafter.

First, a first vehicle type information indicating a type of the vehicle, such as a compact vehicle, a standard-sized vehicle or a truck, is inputted into the external operation device 3 by operating buttons (not shown) of the external operation device 3. When the external operation device 3 is instructed to transmit the inputted first vehicle type information, the first vehicle type information is transmitted from the external operation device 3 to the main device 2.

When the main device 2 receives the first vehicle type information from the external operation device 3, the central control unit 20 renews the first vehicle type information of the operation information stored in the external memory to the first vehicle type information newly received. Then, the main device 2 transmits a notification to notify a completion of renewing of the first vehicle type information in the memory to the external operation device 3.

Next, a second vehicle type information indicating a type of the vehicle, such as a right-hand drive vehicle or a left-hand drive vehicle, is inputted into the external operation device 3 by operating the buttons of the external operation device 3. When the external operation device 3 is instructed to transmit the inputted second vehicle type information, the second vehicle type information is transmitted from the external operation device 3 to the main device 2.

When the main device 2 receives the second vehicle type information from the external operation device 3, the central control unit 20 renews the second vehicle type information of the operation information stored in the external memory to the second vehicle type information newly received. Then, the main device 2 transmits a notification signal to notify a completion of renewing of the second vehicle type information in the memory to the external operation device 3.

Next, when the determination information is inputted into the external operation device 3 by operating the buttons (not shown) of the external operation device 3, and the external operation device 3 is instructed to transmit the inputted determination information, the determination information is transmitted from the external operation device 3 to the main device 2. Here, the determination information is information for determining which reference information is to be used from the reference information made by operation of the external operation device 3 and the reference information made by operation of the DIP switch 22. When the external operation device 3 is instructed o transmit the inputted determination information to the main device 2, the determination information is transmitted to the main device 2.

When the main device 2 receives the determination information from the external operation device 3, the central control unit 20 renews the determination information stored in the external memory to the determination information newly received. Then, the main device 2 transmits a notification signal for notifying a completion of renewing of the determination information in the memory to the external operation device 3.

Thereafter, when an operation to instruct a termination of renewing of the operation information and the determination information is made through an operation button (not shown) of the external operation device 3, the external operation device 3 transmits a signal for notifying the termination of the renewing to the main device 2.

When the main device 2 receives the signal notifying the termination of the renewing the main device 2 transmits a signal indicating an acknowledgement of the termination (termination notification ACK) that consents to the termination of the operation information renewing process to the external operation device 3.

By the operation described above, the operation information stored before the external operation device 3 receives the operation can be renewed to the operation information according to the operation of the external operation device 3.

<Features of the Driver Monitoring Apparatus>

In the driver monitoring apparatus 1 of the present embodiment, the type of the vehicle to which the driver monitoring apparatus 1 is mounted is specified by operating one of the external operation device 3 and the DIP switch 22. Therefore, the reference information, as the determination references for determining the inattentive drive of the driver, and the imaging information can be flexibly changed according to the type of each vehicle.

Namely, in the driver monitoring apparatus 1 of the present embodiment, the reference information and the imaging information are suitably changed for any type of the vehicle. Therefore, even if the driver monitoring apparatus 1 of the present embodiment is used in any type of vehicle, the inattentive drive of the driver is properly determined and warned.

In the case where the reference information and the imaging information are set by operating the DIP switch 22, it is possible to recognize whether the reference information and the imaging information are suitable to the type of the vehicle to which the driver monitoring apparatus 1 is mounted at one view by checking which type of the vehicle the DIP switch 22 indicates.

Also, the reference information and the imaging information can be renewed by operating the external operation device 3. Namely, the reference information and the imaging information can be renewed without touching the main device 2. Therefore, even if the main device 2 of the driver monitoring apparatus 1 is mounted to a position where the main device 2 is difficult to be detached or reached, the reference information and the imaging information can be easily renewed, Further, in the inattentive drive monitoring process, the imaging information is suitably set before S20 according to the type of the vehicle to which the driver monitoring apparatus 1 is mounted. Therefore, the near-infrared light is applied to the driver's face with a brightness approximate to a suitable brightness according to the type of the vehicle, and the camera 4 can capture an image of the driver's face at a zoom factor approximate to a suitable zoom factor.

Therefore, in the process on and after S20 (e.g., S28, S29), the zoom factor of the camera 4 and the brightness of the near-infrared light of the light 5 can be smoothly set to the suitable factor and the brightness. Therefore, even immediately after the driver monitoring apparatus 1 is mounted to a different type of the vehicle, monitoring of a driver, such as monitoring of an inattentive drive, can be smoothly started.

(Correspondence Relationship)

The camera 4, the light 5, and S21 and S23 performed by the central control unit 20 correspond to a detection section.

The information regarding the eye direction calculated at S23 corresponds to a detection information. S24 and S25 performed by the central control unit 20 correspond to a warning section.

The external operation device 3, the DIP switch 22, and S16 and S18 performed by the central control unit 20 correspond to a changing operation section. The RAM 20b corresponds to a storage section. Further, the external operation device 3 corresponds to a receiving device, and the communication IC 23 corresponds to a communication coupling device.

S21 corresponds to an analysis section. S28 and S29 correspond to an imaging information changing section, (Other Embodiments)

The external operation device 3 may be a device dedicated to the drive monitoring apparatus 1, or may be any other device such as a cell phone. In a case where the external operation device 3 is a cell phone, a program for setting the reference information may be installed by downloading from a specific site. Further, the program for setting the reference information may be installed by any other ways.

In the embodiment described above, the external operation device 3 and the main device 2 are exemplarily coupled by the wireless communication. As another example, the external operation device 3 and the main device 2 may be coupled through a wire. That is, a wire communication may be performed between the external operation device 3 and the main device 2.

In the embodiment described above, the driver monitoring apparatus 1 includes both the DIP switch 2 and the external operation device 3 as the changing operation section for changing the reference information and the imaging information according to the type of the vehicle. However, it is not always necessary that the changing operation section includes both of the DIP switch 2 and the external operation device 3. One of the DIP switch 2 and the external operation device 3 may be included in the changing operation section.

Also, a plurality of the DIP switches 2 or a plurality of the external operation devices 3 may be included in the changing operation section.

The camera 4 is not limited to the CMOS camera, but may be any camera, such as COD camera, which can be used for monitoring the eye direction and the face direction of the driver.

In the embodiment described above, the inattentive drive is determined by detecting the eye direction of the driver. As another example, the inattentive drive may be determined based on the face direction of the driver. As further another example, the inattentive drive may be determined based on a combination of the face direction and the eye direction of the driver.

In the embodiment described above, the threshold (e.g., the angle of the eye direction looking at the side mirror) for determining the inattentive drive of the right and left direction of the driver is set as the reference information based on the operation information stored in the external memory. In addition to or alternative to the above, a threshold for determining the inattentive drive in the up and down direction may be set based on the elevation information (Figs, 8A and 8B) and the like.

Figure 8B:
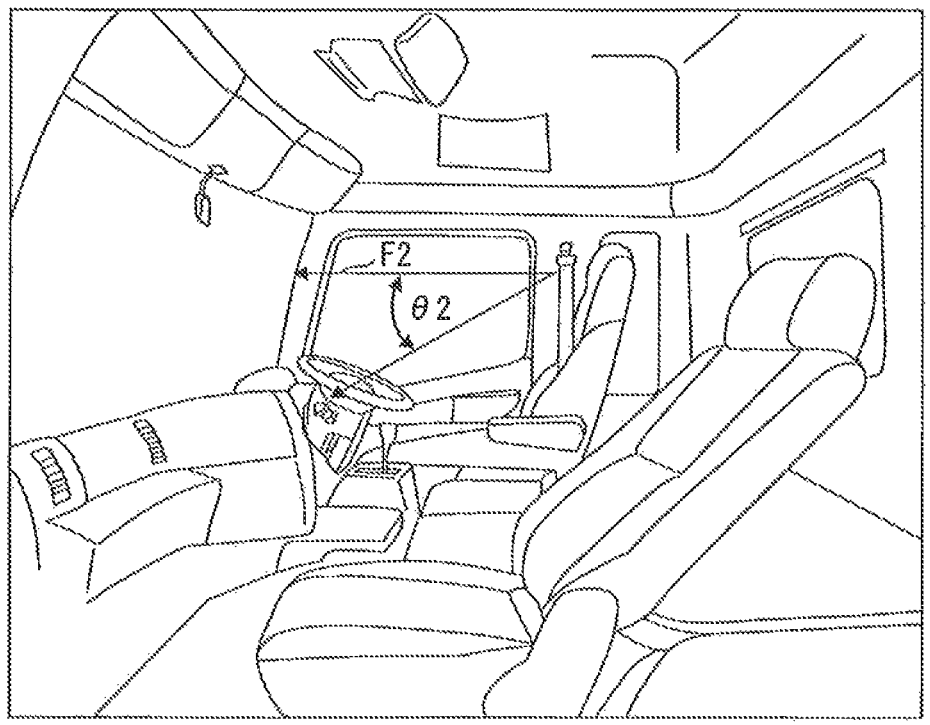
FIG. 8B is a schematic diagram of an image of an interior of a truck for explaining an elevation angle of imaging information and a determination threshold for an inattentive drive in a vertical direction.

In such a case, as shown in FIG. 8A, a threshold ($\theta 1$) for the compact vehicle and the standard-sized vehicle may be set to approximately 20 degrees relative to a horizontal direction F2, which is the same as the elevation information, and corresponds to an angle when the driver sees a meter of an instrument panel, for example. As shown in FIG. 8B, a threshold ($\theta 2$) for the truck may be set to approximately 30 degrees relative to the horizontal direction F2, for example. However, the threshold is not limited to these examples.

In general, with regard to the truck, the position of the driver's face from a meter of an instrument panel is higher than those in the compact vehicle and the standard-sized vehicle. Therefore, the threshold may be different between the compact vehicle and standard-sized vehicle and the truck.

In the embodiment described above, the type of the vehicle is classified into the truck, the standard-sized vehicle and the compact vehicle. The type of the vehicle may be classified more in detail, such as a large truck, a middle truck, and a small truck in the truck; a small-sized vehicle, a middle-sized vehicle, a large-sized vehicle as the standard-sized vehicle; and the like.

In the embodiment described above, the imaging information and the reference information stored in the ROM 20b are renewed according to the operation of the external operation device 3 or the DIP switch 2. In such a case, a configuration to change the imaging information and the reference information is simplified. However, the imaging information and the reference information may be changed separately.

While only the selected exemplary embodiments have been chosen to illustrate the present disclosure, it will be apparent to those skilled in the art from this disclosure that various changes and modifications can be made therein without departing from the scope of the disclosure as defined in the appended claims. Furthermore, the foregoing description of the exemplary embodiments according to the present disclosure is provided for illustration only, and not for the purpose of limiting the disclosure as defined by the appended claims and their equivalents.

What is claimed is:

1. A driver monitoring apparatus for determining an inattentive drive of a driver, the driver monitoring apparatus comprising:

a detection section that detects at least one of a face direction and an eye direction of the driver, and generates a detection information regarding the at least one of the face direction and the eye direction detected;

a warning section that determines whether the driver has the inattentive drive by comparing the detection information to a reference information, and generates a warning when it is determined that the driver has the inattentive drive;

a changing operation section that receives an operation for changing the reference information, and changes a current reference information set before receiving the operation to a new reference information according to the operation received; and wherein the reference information is a vehicle type information.

2. The driver monitoring apparatus according to claim 1, wherein the changing operation section includes a plurality of switches, and the operation for changing the reference information includes operations of the plurality of switches, and the current reference information is changed to the new reference information according to a combination of operated states of the plurality of switches.

3. The driver monitoring apparatus according to claim 2, wherein the current reference information has been set also according to a combination of operated states of the plurality of switches.

4. The driver monitoring apparatus according to claim 1, further comprising:

a storage section that stores the reference information, wherein the changing operation section includes:

a receiving device that receives the operation for changing the reference information; and a communication coupling device that communicably couples the storage section and the receiving device, and when the receiving device receives the operation for changing the reference information, the current reference information stored in the storage section is changed to the new reference information according to the operation that the receiving device receives.

5. The driver monitoring apparatus according to claim 1, wherein the detection section includes:

a light that applies a near-infrared light to a face of the driver;

a camera that captures an image of the face of the driver applied with the near-infrared light; and an analysis section that analyzes the image of the face captured by the camera based on an imaging information including a brightness information regarding a brightness of the light and a zoom factor information regarding a zoom factor of the camera, and the detection section detects the at least one of the face direction and the eye direction of the driver based on an image analyzed by the analysis section, the driver monitoring apparatus further comprising:

an imaging information changing section that changes a current imaging information to a new imaging information based on an analysis result of the analysis section, to obtain a more accurate analysis result than the analysis result obtained before the imaging information is changed.

6. The driver monitoring apparatus according to claim 5, wherein the imaging information further includes an elevation angle information regarding an elevation angle of the camera disposed in a vehicle.

7. The driver monitoring apparatus according to claim 5, wherein the changing operation section receives the operation not only for changing the reference information but also for changing the imaging information, and changes the imaging information according to the operation received.

8. The driver monitoring apparatus according to claim 1, wherein the reference information includes a vehicle type information regarding a type of the vehicle to which the driver monitoring apparatus is equipped, the operation for changing the reference information includes an operation for changing the vehicle type information, and the changing operation section changes a current vehicle type information set before receiving the operation for changing the reference information to a new vehicle type information according to the operation for changing the reference information.

9. A driver monitoring apparatus for determining an inattentive drive of a driver, the driver monitoring apparatus comprising:

a detection section that detects at least one of a face direction and an eye direction of the driver, and generates a detection information regarding the at least one of the face direction and the eye direction detected;

a warning section that determines whether the driver has the inattentive drive by comparing the detection information to a reference information, and generates a warning when it is determined that the driver has the inattentive drive; and an operation section that receives an operation for setting the reference information, and sets the reference information according to the operation received, the reference information being different depending on a type of a vehicle to which the driver monitoring apparatus is equipped.

10. The driver monitoring apparatus according to claim 9, wherein the detection section includes:

a light that applies a near-infrared light to a face of the driver;

a camera that captures an image of the face of the driver applied with the near-infrared light; and an analysis section that analyzes the image of the face captured by the camera based on an imaging information including a brightness information regarding a brightness of the light and a zoom factor information regarding a zoom factor of the camera, and the detection section detects the at least one of the face direction and the eye direction of the driver based on an image analyzed by the analysis section, the driver monitoring apparatus further comprising:

an imaging information changing section that changes the imaging information based on an analysis result of the analysis section to obtain a more accurate analysis result than the analysis result obtained before the imaging information is changed.

11. The driver monitoring apparatus according to claim 10, wherein the imaging information further includes an elevation angle information regarding an elevation angle of the camera disposed in the vehicle.

12. The driver monitoring apparatus according to claim 10, wherein the operation section receives the operation not only for setting the reference information but also for setting the imaging information according to the operation received, the imaging information being different depending on the type of the vehicle.

\* \* \* \* \*